(12) United States Patent
Fumiyama et al.

(10) Patent No.: US 6,398,955 B1
(45) Date of Patent: Jun. 4, 2002

(54) BLOOD FILTER

(75) Inventors: Hideo Fumiyama, Tokyo; Takeshi Aizawa, Yokohama, both of (JP)

(73) Assignee: Jostra Bentley, Inc., Anasco, PR (US)

( * ) Notice: Subject to any disclaimer, the term of this patent is extended or adjusted under 35 U.S.C. 154(b) by 0 days.

(21) Appl. No.: 09/763,517

(22) PCT Filed: Aug. 23, 1999

(86) PCT No.: PCT/US99/19143

§ 371 (c)(1),
(2), (4) Date: Feb. 23, 2001

(87) PCT Pub. No.: WO00/10682

PCT Pub. Date: Mar. 2, 2000

(30) Foreign Application Priority Data

Aug. 24, 1998 (JP) ............................................ 10-237837

(51) Int. Cl.⁷ ................................................ A61M 1/38
(52) U.S. Cl. ...................... 210/304; 210/436; 210/188; 96/212; 96/220; 604/6.09
(58) Field of Search .................... 96/212, 220; 210/188, 210/436, 304; 604/6.09

(56) References Cited

U.S. PATENT DOCUMENTS

| 5,618,425 A | 4/1997 | Mitamura et al. | ....... 210/493.5 |
|---|---|---|---|
| 5,632,894 A | 5/1997 | White et al. | ................. 210/436 |
| 5,782,791 A * | 7/1998 | Peterson et al. | ................ 604/4 |

FOREIGN PATENT DOCUMENTS

WO     WO 96 33770 A     10/1996

* cited by examiner

*Primary Examiner*—James Ketter
(74) *Attorney, Agent, or Firm*—Christie, Parker & Hale, LLP

(57) ABSTRACT

A blood filter (1) has a small priming volume and a high ability of trapping and removing the air bubbles. The blood filter (1) according to the present invention includes a housing (5) accommodating a blood inlet (8), a blood outlet (9), an air bubble outlet (14), and a filter element (3) disposed in the housing (5). The blood inlet (8) is preferably disposed in the vicinity of a bottom surface (7) of the housing. The housing (5) includes a spiral chamber (10) defined between an inner wall (5b) and an outer wall (5a) of the housing (5) and a center chamber (11) defined within the inner wall (5b). The spiral chamber (10) extends in a helix shape to surround the center chamber (11). Due to such a structure, even when air bubbles are introduced to the blood filter (1) through the blood inlet (8), the air bubbles are effectively separated from the blood in the spiral chamber (10). The blood filter having such a spiral chamber (10) is unlikely influenced by the blood flow rate and the amount of air bubbles. It has a high ability of removing the air bubbles at a high flow rate despite a small priming volume and it has a sufficiently small pressure loss.

13 Claims, 10 Drawing Sheets

BLOOD FILTER

CROSS-REFERENCE TO RELATED APPLICATION

This application claims priority of International application number PCT/US99/19143, filed Aug. 23, 1999, which in turn claims priority to Japanese patent application number 10-237837, filed Aug. 24, 1998.

BACKGROUND OF THE INVENTION

1. Field of the Invention

The present invention relates to a blood filter used for forming an extracorporeal circulation circuit for extracorporeally circulating bodily fluids such as blood in, for example, an artificial cardiopulmonary system and an artificial kidney system. More particularly, the present invention relates to a blood filter for removing foreign substances, thrombus and air bubbles in an extracorporeal circulation circuit.

2. Description of Related Art

Extracorporeal circulation of bodily fluid such as blood is generally applied to patients who require heart surgery or artificial dialysis. In extracorporeal circulation in heart surgery, the patient's blood is guided outside the body and treated by an artificial cardiopulmonary system provided outside the patient's body, and the treated blood is returned to the body. Extracorporeal circulation is generally performed using an extracorporeal circulation circuit including a chamber (or blood reservoir), a blood pump, an artificial lung, a filter and a tube.

One serious problem in extracorporeal circulation of blood is formation of a thrombus. A thrombus is formed by contact of the blood with a foreign substance, such as air bubbles mixed in the extracorporeal circulation circuit or a tube included in the extracorporeal circulation circuit. Specifically, the air mixed in the extracorporeal circulation circuit activates a blood coagulation system and promotes formation of the thrombus. Accordingly, an extracorporeal circulation circuit generally includes a device for removing air bubbles mixed therein. Usually, the air bubbles mixed in the extracorporeal circuit are primarily removed in a blood reservoir. The thrombus is also formed by contact of blood and a foreign substance, such as a plastic material used for the extracorporeal circulation circuit.

In order to remove the air bubbles mixed in the extracorporeal circulation circuit, an open-type blood reservoir is in a wide use, which is easy to operate and has a high air bubble removing ability. The open-type blood reservoir includes a region of air therein so as to provide a large contact area between the blood and the air. Due to such a structure, the air bubbles mixed in the extracorporeal circulation circuit is moved to the region of air with certainty and thus the air is removed from the extracorporeal circulation circuit A closed-typed reservoir having no region of air therein has also been developed and marketed. It is difficult to remove air bubbles completely from the extracorporeal circulation circuit which circulates a large amount of blood and includes either type of blood reservoir. Thus, the air bubbles which have not been removed in the blood reservoir are trapped by a blood filter and removed before returning to the patient's body.

Foreign substances derived, for example, from the tube, blood pump or artificial lung included in the extracorporeal circulation circuit can also be mixed in the extracorporeal circulation circuit.

The thrombus and the foreign substances contained in the extracorporeal circulation circuit are generally removed by a blood filter in a final stage of the extracorporeal circulation circuit before the blood is returned to the patient's body.

The blood filter for removing air bubbles and thrombus contained in the extracorporeal circulation circuit is required to have a minimum possible volume while maintaining a low pressure loss with respect to the blood flow rate required for the extracorporeal circulation circuit and in order to minimize the priming volume in the extracorporeal circulation circuit. When the priming volume of the blood filter is reduced, however, the ability of removing the air bubbles, the thrombus and the other foreign substances is lowered and the pressure loss is increased.

Especially in recent cardiovascular surgery, it has been actively attempted to minimize surgical invasion to the patient so as to promote recovery and minimize side effects on the patient. One type of maneuver referred to as minimally invasive surgery has been developed. It has also been actively attempted to minimize the priming volume in the extracorporeal circulation circuit so as to farther suppress the side effects caused by the dilution of the blood and blood transfusion. In accordance with such trends, the components incorporated in the extracorporeal circulation circuit are now required to be a further reduced in size and volume.

Conventionally, the extracorporeal circulation temperature of the blood during surgery is usually maintained low for the purpose of reducing oxygen consumption by the patient However, a low temperature leads to increased operation time due to the extended time needed to re-raise the temperature of the blood to normal body temperature and organopathy is caused by low temperature circulation. Thus, it has been actively attempted to maintain the temperature of extracorporeally circulating blood at a level which is as close as possible to the body temperature. This helps to minimize invasion to the patient, as well as shorten the operation time. In the case where the blood temperature is maintained low, the extracorporeally circulating blood needs to be set in a larger amount than is required by the consumption by the brain and main organs of the patient during the surgery. Accordingly, the components in the extracorporeal circulation circuit need to maintain a sufficiently high performance even with a high flow rate of blood.

Under the circumstances, a blood filter which is compact and still has a sufficiently high removing ability of air bubbles, thrombus and foreign substances and a low pressure loss even with a high flow rate of blood has been demanded.

SUMMARY OF THE INVENTION

The present invention has an objective of improving the conventional blood filter used for an extracorporeal circulation circuit and providing a blood filter which eliminates the problems unsolved by the conventional technology and handles the above-described new method of surgery. In other words, the present invention has an objective of providing a blood filter which is a compact and still has a sufficiently high removing ability of air bubbles, thrombus and foreign substances and a sufficiently low pressure loss even with a high flow rate of blood.

In order to achieve the above-described objective, the blood filter according to the present invention includes a housing having a spiral chamber with a blood inlet at one end thereof, preferably in the vicinity of a bottom surface of the housing. The spiral chamber is defined between a partially cylindrical spiral-shaped inner wall and a cylindrical outer wall of the blood filter housing and extends along the inner wall of the housing.

More specifically, the blood filter of the present invention comprises: a housing accommodating a blood inlet, a blood outlet, an air bubble outlet; an inner wall, an outer wall, and a filter element disposed in the housing. The filter element divides an inner space of the housing into a first space which is in communication with the blood inlet and a second space which is in communication with the blood outlet. The first space includes a center chamber defined within the inner wall of the housing and a spiral chamber defined between the inner wall and the outer wall of the housing and extending along the inner wall of the housing. The spiral chamber has the blood inlet at one of two ends hereof and an opening at the other end thereof which is in communication with the center chamber. The center chamber has the air bubble outlet. The spiral chamber has an inner bottom surface and an inner top surface which define a spiral passage extending upwardly from the blood inlet to the opening. The spiral passage is disposed to substantially surround the center chamber.

The inner bottom surface of the spiral chamber may extend along a perimeter of a bottom surface of the housing. An inner surface of the filter element which faces the second space and a part of an inner surface of the housing defines a lengthy passage which has the blood outlet at one end thereof and extends perpendicular to the inner bottom surface of the spiral chamber.

Preferably, the spiral passage of the spiral chamber surrounds the center chamber in the range of 180 degrees to 400 degrees.

Preferably, an apex of the inner top surface of the spiral chamber, the apex being in the vicinity of the opening, is at a higher level than the filter element.

Preferably, the spiral passage of the spiral chamber has a cross-section which increases from the blood inlet to the opening.

Preferably, the spiral passage of the spiral chamber has a cross-section which increases so that a blood velocity at the opening is ½ or less of a blood velocity at the blood inlet.

Preferably, the inner top surface of the spiral chamber extends from the blood inlet to the opening in a direction away from the inner bottom surface of the spiral chamber.

Preferably, the inner top surface of the spiral chamber extends at an angle in the range of 5 degrees to 60 degrees with respect to the inner bottom surface of the spiral chamber.

Preferably, the distance between the apex of the inner top surface of the spiral chamber in the vicinity of the opening and the inner bottom surface of the spiral chamber may be about 4 times or more the width of the spiral chamber in a radial direction of the housing.

The center chamber may have a sub chamber and the air bubble outlet may be disposed at an apex portion of the sub chamber.

Preferably, the sub chamber has a volume which is 1/100 to 1/10 of the volume of the center chamber.

Preferably, the filter element is disposed in the center chamber in such a manner that the center axis of the filter element does not correspond to the center axis of the center chamber.

DETAILED DESCRIPTION OF THE INVENTION

Figure 1:
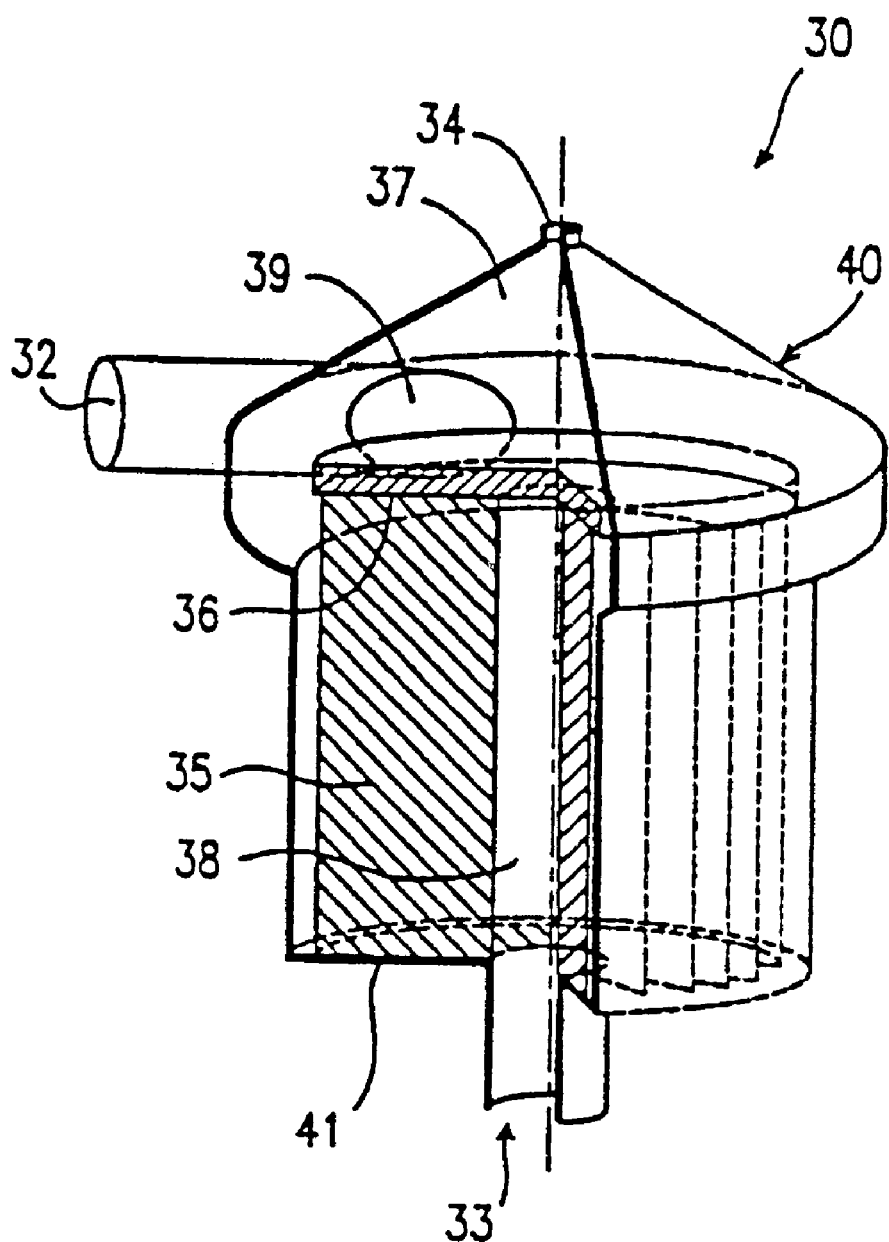
FIG. 1 is a view illustrating a conventional blood filter.
Figure 2:
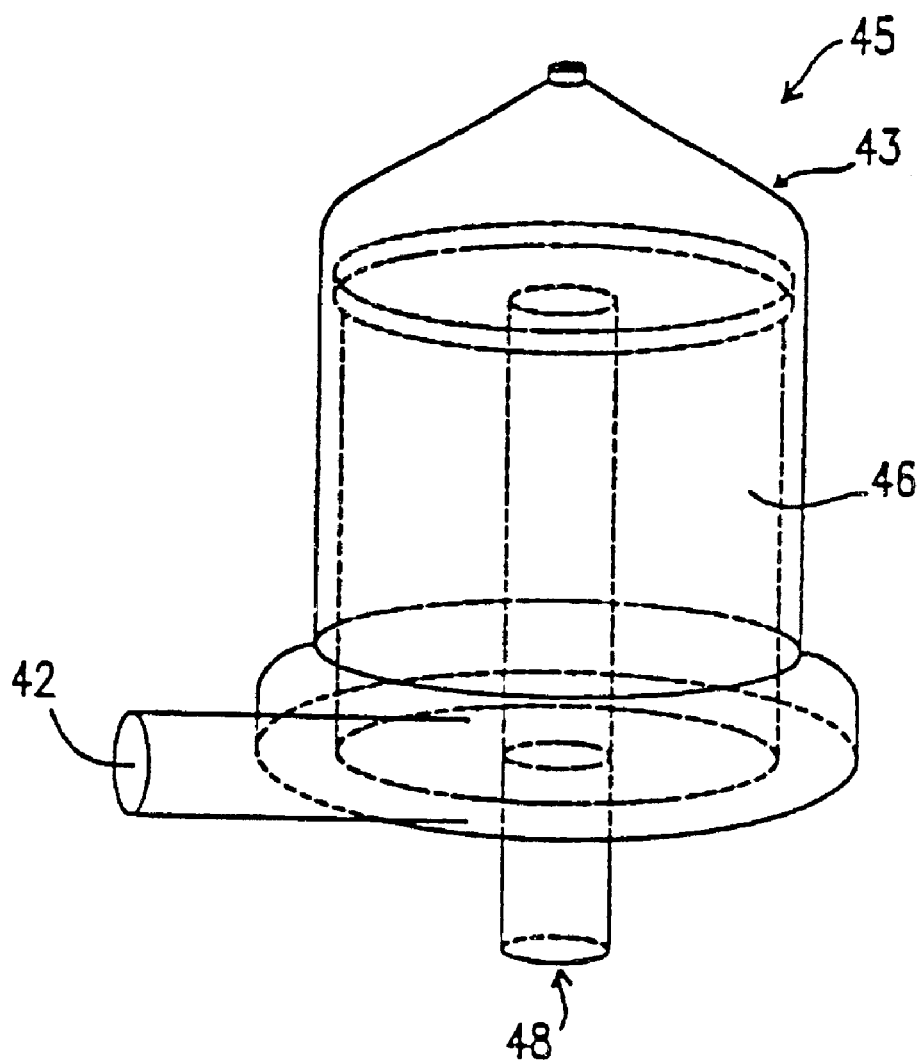
FIG. 2 is a view illustrating another conventional blood filter.

FIGS. 1 and 2 show two representative types of conventional blood filters. The conventional blood filter 30 shown in FIG. 1 is characterized in that the blood inlet 32 is disposed in a top portion of the blood filter housing 40. A convention blood filter 45 shown in FIG. 2 is characterized in that a blood inlet 42 is disposed in a bottom portion of a blood filter housing 43 in order to overcome some of the drawbacks of t conventional blood filter a shown in FIG. 1. The either of the blood filters shown in FIGS. 1 and 2, it is difficult to achieve size reduction while maintaining the sufficient removing ability of the air bubbles, thrombus and foreign substances, due to the structures thereof. The structural drawbacks of these blood filters will become clearer after the operation thereof in two separate cases is explained, i.e., when a relatively small amount of air bubbles (1 ml to 5 ml) are introduced and a relatively large amount of air bubbles (20 ml or more) are introduced.

FIG. 1 shows a conventional blood filter 30. The blood guided outside the patient's body and treated by the blood reservoir and the artificial lung is directed into the blood filter 30 through a blood inlet 32 and introduced to a filter element 35 disposed in a housing 40 through an opening 39. The opening 39 is in communication with a first space 37 which surrounds the filter element 35. The filter element 35 is usually formed of a bellow-shaped screen mesh material and originally stored similar to a compressed accordion. Two ends of the bellow-shaped material are extended outward like an opened accordion and bonded together to form a cylindrical shape having a passage therein. A cap 36 is provided on a top surface of the filter element 35. The blood contacts a side surface of the filter element 35 and flows into a second space 38 through the filter element 35. The second space 38 is formed of the passage surrounded by the filter element 35. Then, the blood is released from the blood filter 30 through a blood outlet 33. The filter element 35 is provided with the cap 36 on the top surface thereof as described above, and a bottom surface of the filter element 35 is in contact with a bottom surface 41 of the housing 40. Accordingly, the blood flows into the second space 38 only through the side surface of the filter element 35. The air bubbles mixed in the blood are separated from the blood in the first space 37 and released through an air bubble outlet 34. Thus, the air bubbles are removed from the extracorporeal circulation circuit.

When a relatively small amount of blood is introduced into the conventional blood filter 30 as shown in FIG. 1 having the blood inlet 32 in a top portion of the blood filter housing 40, the amount of air bubbles effectively released through the air bubbles outlet 34 directly depends on the volume of a portion of the housing 40 above the blood inlet 32. In other words, when a small amount of air bubbles are introduced into the blood filter 30 in the state where the portion of the blood filter housing 40 above the blood inlet 32 is filled with blood, the air bubbles are movable upward in the housing 40 relatively easily and stay in an apex portion of the housing 40. The amount of air bubbles which can stay in the blood filter housing 40 above the blood inlet 32 is equal to the volume of the portion of the filter housing 40 above the blood inlet 32 at maximum. The excess air bubbles are transported by the blood. Such air bubbles partially reach a portion of the housing 40 below the opening 39 and are released through the blood outlet 33 after passing through the filter element 35. Such a phenomenon occurs more often as the amount of blood increases (especially, when the blood flow rate is 6L/min. or more) and is very undesirable in terms of the air bubbles removing ability.

The structural drawbacks of the conventional blood filter 30 as shown in FIG. 1 become clearer when a relatively large amount of air bubbles are introduces into the blood filter 30. When a large amount of air bubbles are introduced into the blood filter 30, a blood phase and an air bubble phase are generated in the blood filter housing 40 in accordance with the amount of air bubbles introduced. The blood phase is generated in the bottom portion of the housing 40, and the air bubble phase is generated in the top portion of the housing 40. When the extracorporeal circulation continues in this state, the blood is introduced into the air bubble phase in the blood filter housing 40 through the blood inlet 32. Accordingly, the blood flows while the air is stirred, thus generating a great amount of microbubbles.

The generation of the great amount of microbubbles mixes the air and the liquid to such an extent that the border between the air bubbles phase and the blood phase is not recognizable by the naked eye, although the housing 40 is generally formed of a transparent plastic material. This is very undesirable for the clinical use of the blood filter 30. Due to such a phenomenon, a part of the microbubbles partially move from the first space 37 to the second space 38 and then are released through the blood outlet 33. This is very dangerous to the patient In an ideal blood filter, even when a large amount of air bubbles are introduced, the microbubbles released through the blood outlet are restricted to a minimum possible amount. In the conventional blood filter 30 having the blood inlet 32 in the top portion of the blood filter housing 40, the blood cannot avoid passing through the air phase in the blood filter housing 40 due to the structure thereof Accordingly, the mixture of air and the blood is unavoidable and so is generation of a large amount of microbubbles.

For the purpose of solving the structural drawbacks of the conventional blood filter 30 as shown in FIG. 1, the blood filter 45 as shown in FIG. 2 has conventionally been proposed and marketed. The blood filter 45 includes the blood inlet 42 in the bottom portion of the blood filter housing 43.

The characteristics of the conventional blood filter 45 as shown in FIG. 2 regarding the air bubbles mixed in the blood will become clearer after the operation thereof in two separate cases is explained, i.e., when a relatively small amount of air bubbles (1 ml to 5 ml) is introduced and a relatively large amount of air bubbles (20 ml or more) is introduced, as in the case of the conventional blood filter 30 shown in FIG. 1.

When a relatively small amount of air bubbles is introduced into the conventional blood filter 45 as shown in FIG. 2 and when the flow rate of blood is relatively low, for example, 5L/min. or less, phenomena causing serious problems do not occur. When the flow rate is raised the blood begins whirling in the bottom portion of the housing 43 due to the high inertia thereof. The air bubbles having a small buoyancy are affected by the inertial force and cannot be moved upward in the housing 40. The air bubbles are partially released through a blood outlet 48 after passing through a filter element 46. Accordingly, the conventional blood filter 45 as shown in FIG. 2 has a disadvantage of not being suitable for air bubble removal when the flow rate of the blood is high.

Next, the operation performed when a relatively large amount of air bubbles is introduced into the conventional blood filter 45 as shown in FIG. 2 will be described below. Unlike the conventional blood filter 30 of FIG. 1, the conventional blood filter 45 as shown in FIG. 2 allows the blood to be introduced from the blood inlet 42 provided in the bottom portion of the blood filter housing 43 to the blood phase in the blood filter housing 43 with certainty, even when a large amount of air bubbles are introduced to the blood filter 45. Accordingly, mixing of the blood with the air bubbles is suppressed, and thus microbubbles are not likely to be generated compared to the case of the blood filter 30 as shown in FIG. 1. However, the blood filter 45 having such a structure cannot avoid generation of microbubbles when the amount of air bubbles introduced thereinto exceeds a certain level.

One index representing the relationship between the amount of air bubbles introduced into a blood filter at one time and the amount of microbubbles released from an outlet of the blood filter is "break-out threshold". As used therein, the term "break-out threshold" represents the maximum possible amount of air bubbles which can be introduced into a blood filter at one time while the amount of microbubbles released from the he outlet of the blood filter is maintained at a certain level or less (tolerable range). In other words, when an amount of air bubbles exceeding the break-out threshold are introduced into the blood filer at one time, the excess air bubbles are released from the blood outlet in the form of microbubbles. Accordingly, blood filters are more desirable when their break-out thresholds are higher.

In the case of the conventional blood filter 45 as shown in FIG. 2, the volume (priming volume) is generally in proportion to the break-out threshold. A higher break-out threshold requires a larger volume of the blood filter 45, which makes size reduction difficult.

When a relatively large amount of air bubbles is introduced into the blood filter housing 43 of the blood filter 45, the number of opportunities of the air bubbles directly contacting the filter element 46 increases. Thus, the air bubbles are divided into smaller air bubbles. Such a phenomenon lowers the air bubble removing ability and is disadvantageous in raising the break-out threshold.

When an equal amount of air bubbles is introduced into the blood filter 30 as shown in FIG. 1 and the blood filter 45 as shown in FIG. 2, a larger amount of microbubbles are generated in the blood filter 30 due to the mixture of the air bubble phase and the blood phase than in the blood filter 45. Accordingly, release of the microbubbles through the blood outlet 33 is unavoidable. In consequence, the break-out threshold of the blood filter 30 is low with respect to the volume thereof The present invention made in light of the issues associated with the conventional filters as shown in FIGS. 1 and 2, has an objective of providing a blood filter which is compact but has a sufficiently high removing ability of air bubbles, thrombus and foreign substances while maintaining the pressure loss at a low level even with a high flow rate of blood and also has a sufficiently high break-out threshold.

Figure 3:
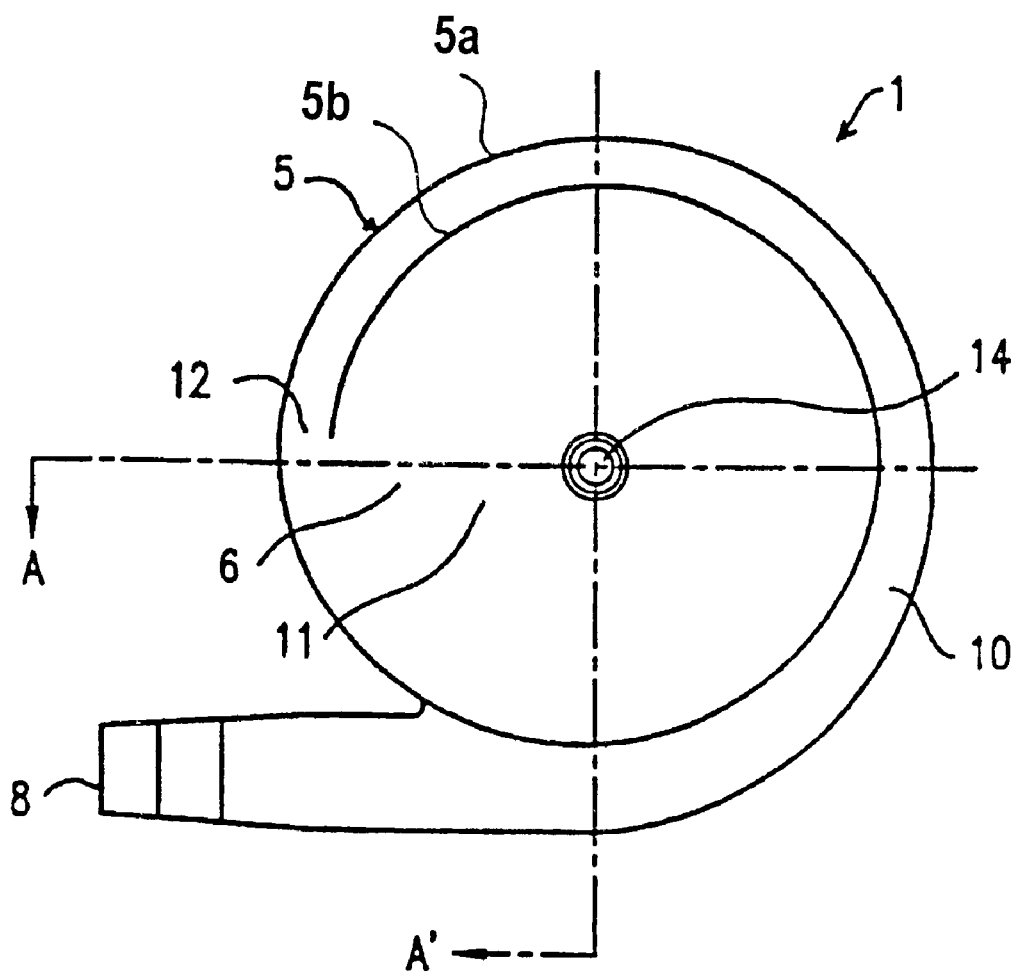
FIG. 3 is a plan view of an examplary blood filter according to the present invention.
Figure 4:
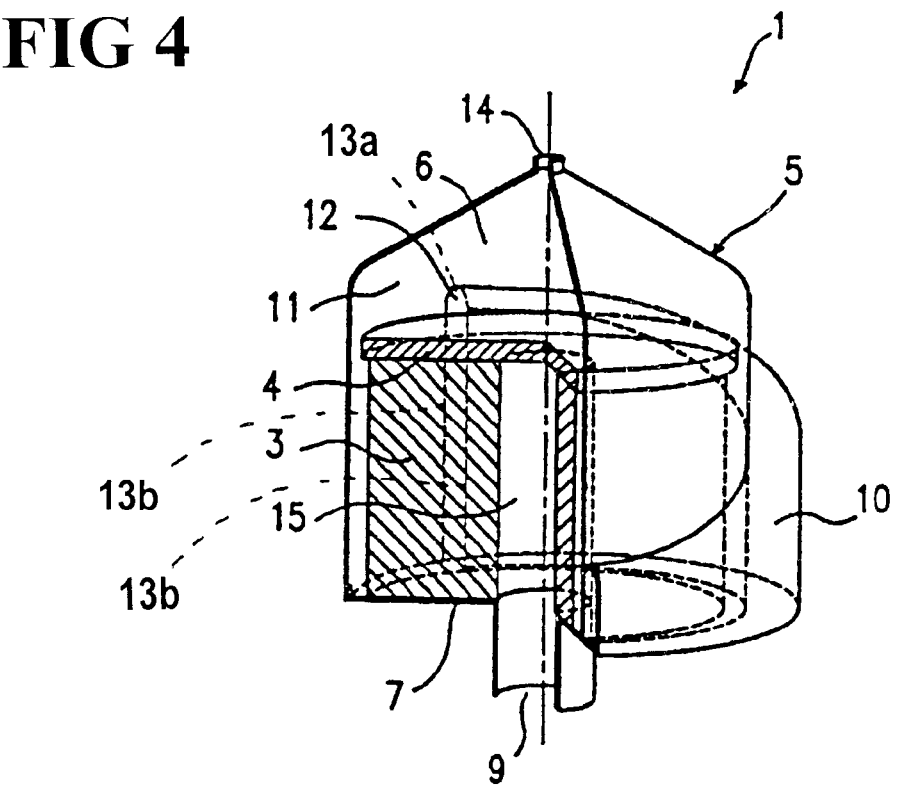
FIG. 4 is a perspective partial cross-sectional view of the blood filter of the present invention taken along line A—A' in FIG. 3.

FIGS. 3 and 4 show one preferred example of the present invention. FIG. 3 is a plan view of a blood filter 1 according to the present invention. FIG. 4 is a perspective partial cross-sectional view of the blood filter 1 taken along lines A—A' in FIG. 3.

Referring to FIGS. 3 and 4, the blood guided outside the patient's body passes through a blood reservoir, an artificial lung and the like (not shown) and then is directed into a spiral chamber 10 of the blood filter 1 through a blood inlet 8. The blood inlet 8 is located at the one of two ends of the spiral chamber 10 while at the other end thereof is located an opening 12 which is in communication with the center chamber 11. The center chamber 11 accommodates a filter element 3, as seen in FIG. 4. The spiral chamber 10 is it in communication with the center chamber 11 through the opening 12. The spiral chamber 10 and the center chamber 11 are separated from each other by the inner wall 5b provided in the housing. An inner space of the housing is divided into a first space 6 accommodating the blood inlet 8 and a region within the housing 5 except for the region surrounded by the filter element 3, and a second space 15 accommodating the region surrounded by the filter element 3 and a blood outlet 9.

The spiral chamber 10 has an inner bottom surface and an inner top surface. The inner bottom surface of the spiral chamber 10 may be part of a bottom surface 7 of a housing 5 and, for example, may extend along a perimeter of the bottom surface 7. The inner top surface of the spiral chamber 10 starts from near the inner bottom surface and continues upward in a helix like shape. The inner bottom surface and the inner top surface of the spiral chamber 10 define a spiral passage of the spiral chamber 10 extending from the blood inlet 8 to an opening 12, which is in communication with a center chamber 11. The opening 12 defines an inverted U-shaped cross-section including a curved portion 13a and two substantially linear sections 13b between a cylindrically shape housing wall (outer wall 5a) and a partially cylindrical spiral-shaped wall (inner wall 5b) of the housing 5, as seen in FIGS. 3 and 4. The spiral chamber 10 extends along the inner wall 5b of the housing 5 while the height thereof increases. Therefore, the height of the spiral chamber 10 increases reaching the distance between the inner bottom surface and the apex of the curved section 13a. Air bubbles mixed in the blood flow along a top part of the spiral chamber 10 while the blood flows in the lower portion of the spiral chamber 10, and thus the air bubbles are separated from the blood When necessary, tile spiral passage of the spiral chamber 10 defined by the inner bottom surface and the inner top surface extends along the perimeter is of the bottom surface 7 of the housing so as to surround the center chamber 11 within the range of 180 degrees to 400 degrees. The inner top surface of the spiral chamber 10 is designed to extend helically upward along the inner wall 5b of the housing at an angle, for example, between about 5 degrees to 60 degrees with respect to the inner bottom surface. Due to such designing, the air bubbles mixed in the blood are effectively separated from the blood in the spiral chamber 10.

The filter element 3 can be the same as the conventional filter element 35 shown in FIG. 1 and is equipped with a cap 4 thereon The blood contacts a side surface of the filter element 3 and flows into the second space 15 through the filter element 3. The second space 15 includes a passage surrounded by the filter element 3. Then, the blood is released from the blood filter 1 through the blood outlet 9. The air bubbles separated from the blood in the spiral chamber 10 are released from the blood filter 1 through an air bubble outlet 14 provided at an apex of the center chamber 11. Thus, the air bubbles are removed from the extracorporeal circulation circuit.

The housing is formed of a material which can withstand a sterilization treatment usually applied to devices used for extracorporeal circulation circuits, for example, a transparent engineering plastic material such as polycarbonate of polypropylene.

The blood filter according to the present invention having the above-described structure operates in the following manner.

The blood introduced to the blood filter through the blood inlet is first guided to the spiral chamber and then flows around the center chamber. The blood flows into the center chamber while the blood velocity thereof is decreasing. The blood guided to the center chamber flows through the filter element and out of the blood filter through the blood outlet. Then, the blood is returned to the patient.

The air bubbles which are introduced to the blood filter through the blood inlet first flow in the spiral chamber. While the blood flows in the spiral chamber, the air bubbles move to the vicinity of the inner top surface of the spiral chamber along the inner wall of the housing due to the function of the centrifugal force and the buoyancy of the air. Furthermore, as the cross-section of the spiral chamber increases from the blood inlet toward the center chamber, the blood flow rate gradually decreases. The decreasing blood flow rate promotes separation of the air bubbles from the blood due to the buoyancy of the air bubbles. In one preferred embodiment, the spiral passage of the spiral chamber has a cross-section which increases so that a blood velocity at the opening is ½ or less of a blood velocity at the blood inlet. The air bubbles are more and more separated from the blood while the blood and air bubbles pass through the spiral chamber. The air bubbles are moved toward the inner top surface of the spiral chamber and the blood is moved toward the inner bottom surface of the spiral chamber.

Accordingly, when the blood flows into the center chamber, the air phase is guided to the air bubble outlet of the blood filter housing. Thus, the air bubbles are effectively separated from the blood. The separation is performed with almost the same effectiveness whether the amount of the air bubbles is large or small. When a small amount of air bubbles are introduced to the blood filter, the air bubbles are moved toward the inner top surface of the spiral chamber while passing through the spiral chamber. When the air bubbles reach the opening of the spiral chamber in communication with the center chamber, the air bubbles move to an apex portion of the center chamber. This is performed in a similar manner when the blood flow rate is high. Thus, the drawback of the conventional blood filters shown in FIGS. 1 and 2 is solved.

When a large amount of air bubbles are introduced to the blood filter, generation of a large amount of microbubbles caused by the air phase being mixed with the blood phase does not occur unlike in the conventional blood filter shown in FIG. 1, since the blood inlet is disposed in the vicinity of the bottom surface of the housing. The spiral chamber allows the air bubbles to be effectively separated from the blood by the function of the centrifugal force and the buoyancy of air while the blood passes through the spiral chamber. Accordingly, the break-out threshold is allowed to be higher with respect to the total priming volume of the blood filter compared to the conventional blood filter having the blood inlet in the bottom portion of the blood filter housing. Thus, the total priming volume of the blood filter is allowed to be very small.

The apex of the inner top surface of the spiral chamber is at a higher level than the filter element in the vicinity of the opening of the spiral chamber in communication with the center chamber. Accordingly, the air bubbles are guided to the air bubble outlet disposed at the apex portion of the center chamber without directly contacting the filter element. Due to such a system, the air bubbles are prevented from becoming microbubbles due to the direct contact of the air bubbles with the filter element. Thus, separation of the air bubbles from the blood is performed more effectively.

The angle of the inner top surface of the spiral chamber with respect to the inner bottom surface thereof can be increased in the vicinity of the opening of the spiral chamber which is in communication with the center chamber. In such a structure, the air bubbles flowing out of the spiral chamber are more easily guided to the air bubble outlet disposed at the apex portion of the center chamber. Thus, separation of the air bubbles from the blood is performed more effectively.

Figure 5:
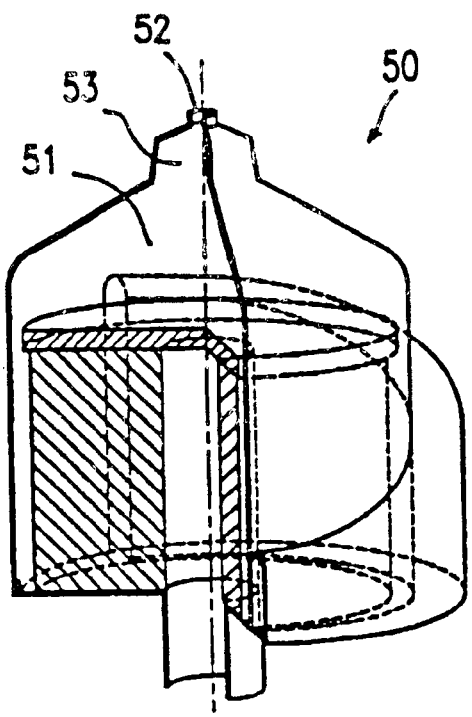
FIG. 5 is a perspective partial cross-sectional view of another alternative embodiment of the blood filter according to the present invention.

FIG. 5 shows a blood filter 50 in an alternative example according to the present invention. In the example shown in FIG. 5, a center chamber 51 includes a sub chamber 53 acting as an air bubble trapping chamber. The sub is chamber 53, which traps the air bubbles separated from the blood in the spiral chamber, reduces the contact area between the separated air bubbles and the blood. Thus, the air bubbles are prevented from being mixed in the blood again. A sub chamber can be provided in a top part of the center chamber, in which case the air bubble outlet 52 is provided at an apex portion of the sub chamber. In such a structure, the air bubbles flowing out of the spiral chamber are stored in the sub chamber instead of a top portion of the center chamber. Due to such a system, the air bubbles once separated from the blood are prevented from being mixed again with the blood flow to be transported to the center chamber. Therefore, generation of microbubbles caused by the contact of the air bubbles with the filter element is prevented. Thus, separation of the air bubbles from the blood is performed more effectively.

Figure 6:
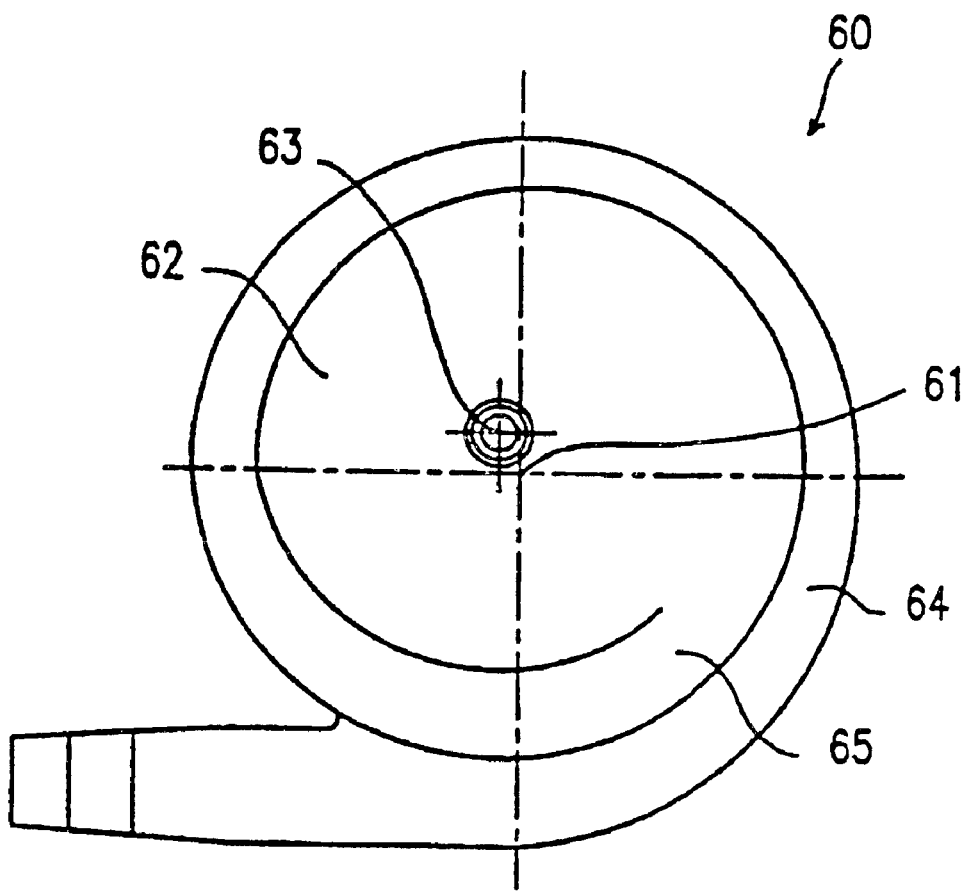
FIG. 6 is a plan view of another examplary blood filter according to the present invention.

FIG. 6 shows a blood filter 60 in another alternative example according to the present invention. In the example shown in FIG. 6, a spiral passage of the spiral chamber 64 has an opening 65 and extends so as to surround the center chamber 62 over about 400 degrees, thereby separating the air bubbles from the blood with more certainty. In this example, the spiral chamber occupies a higher percentage of the space in the housing than in the previous examples. Accordingly, the filter element (not shown) is located so that a central axis 63 of the filter element does not correspond to a central axis 61 of the center chamber 62.

The present invention will be described more specifically with reference to the following illustrative examples.

Figure 7:
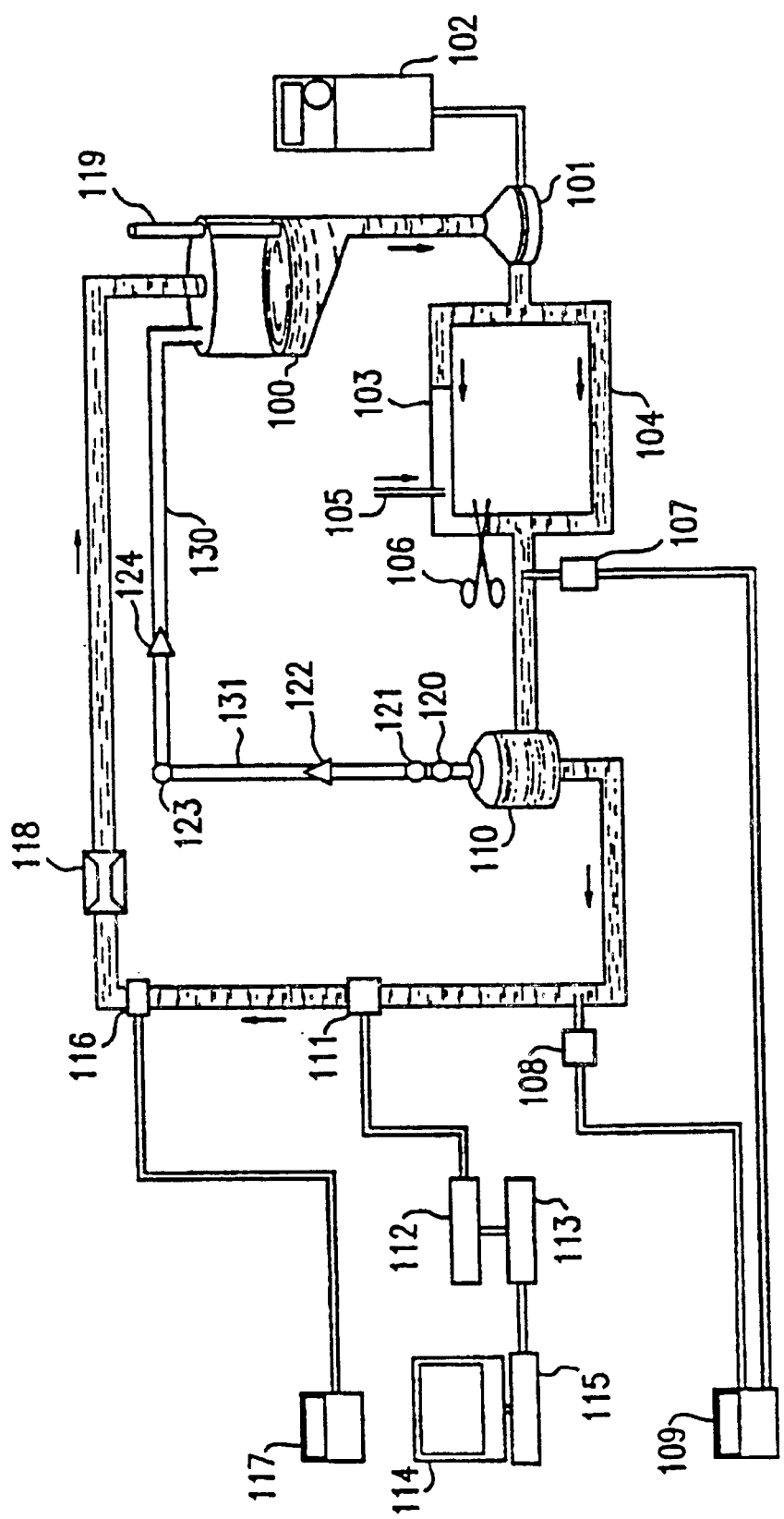
FIG. 7 is a schematic view of an experimental system used for comparison between the blood filter according to the present invention and the conventional blood filters.

The performance of the blood filter according to the present invention was tested in an experimental circuit shown in FIG. 7 using fresh bovine blood (hematocrit: 35%). The experimental circuit shown in FIG. 7 is similar to an extracorporeal circulation circuit.

In FIG. 7, the blood stored in an open-type blood chamber 100 accommodating a thermometer 119 is transported in the direction shown by the arrow through a main tube 104 formed of polyvinyl chloride PVC) by a centrifugal pump 101 and is introduced to a blood filter 110. The flow rate of the blood in the experimental circuit shown in FIG. 7 is adjusted by a centrifugal pump console 102 connected to the centrifugal pump 101. The blood filter 110 is connected to a vent line 130 for introducing air bubbles which have been separated from the blood in the blood filter 110 to a region of air in the blood chamber 100 through two three-way stopcocks 120 and 121, a check valve 122, a one-way stopcock 123 and a check valve 124. When the air bubbles separated in the blood filter 110 are accumulated to a certain amount, the stopcocks 120; 121 and 123 are manually operated to introduce the air bubbles to the region of air in the blood chamber 100. As the filter element in the blood chamber, a commercially available polyethylene terephthalate filter element having a mesh size of about 40 um is used.

The PCV pipes respectively connected to an inlet and an outlet of the blood filter 110, pressure transducers 107 and 108 (for example, pressure transducers VPRNP-A5-(-1 TO 2K)-4 manufactured by Valcom) are disposed to measure a pressure loss caused by the blood chamber 100. A recorder 109 for recording the measurement results is connected to each of the pressure transducers 107 and 108.

The blood which has exited the blood filter 110 flows in the PVC pipes in the direction of the arrow. The amount of microbubbles in the blood and the blood flow rate were measured respectively by a microbubble detection probe 111 (such as, for example, probe CM6-13 manufactured by Hatteland Instrumentering) and an electromagnetic blood flow meter probe 116 (for example, probe FF090T manufactured by Nihon Kodensha). For obtaining the measurement results, the microbubble detection probe 111 is connected to a cardiovascular microbubble detector 112 (for example, CMD10 manufactured by Hatteland Instrumentering), which is connected to a computer 115 and a display 114 through an interface 113. The electromagnetic flow meter probe 116 is connected to an electromagnetic blood flow meter 117 (for example, MFV-3200 produced by Nihon Kodensha). After the measurements are taken, the blood is returned to the blood chamber 100 through an adjustable clamp 118. The cardiovascular microbubble detector 112 detects the size and the number of microbubbles in the blood and outputs the results in a histogram.

The blood filter according to the present invention and the conventional blood filters shown in FIGS. 1 and 2 were set in the above-described experimental circuit and the air bubbles removing ability and the pressure loss of these blood filters were measured. For all the measurements, fresh bovine blood adjusted to have a hematocrit of 35% was used. The parameters of the blood filters tested are shown in Table 1.

TABLE 1

Blood Filters Tested

| Type | Priming Volume | Maximum Flow Rate |
|---|---|---|
| (a) FIG. 4 (present invention) | 155 ml | 7 L/min |
| (b) FIG. 1 (conventional 1) | 207 ml | 7 L/min. |
| (c) FIG. 1 (conventional 2) | 210 ml | 7 L/min. |
| (d) FIG. 2 (conventional) | 250 ml | 6 L/min. |

Blood filter (a) has a structure shown in FIG. 4 according to the present invention. Blood filters (b) and (c) are commercially available and have a blood inlet in a top portion of the blood filter housing as shown in FIG. 1. Blood filters (b) and (c) are set to have a maximum blood flow rate of 7 L/min.

Blood filters which are commercially available currently having a maximum blood flow rate of 7 L/min are only available in two types which are used as blood filters (b) and (c) in this experiment.

Blood filter (d) has a blood inlet in a bottom portion of the blood filter housing as shown in FIG. 2. Such a type of blood filters are currently available only in the types used as blood filter (d) in this experiment. Blood filter (d) has a maximum blood flow rate of 6 L/min.

Test items and conditions performed on blood filters (a), (b), (c) and (d) are shown in Table 2.

TABLE 2

| | test items and conditions Blood Filter | | | |
|---|---|---|---|---|
| Items | (a) | (b) (c) | (d) | Maximum blood flow rate |
| Vent air amount | T | T | T | 6 L/min |
| Break-out threshold | T | T | NT | 7 L/min |
| Pressure loss | T | T | T | 3–7 L/min |

Letter "T" indicates that the test was performed and the letters "NT" indicate that the test was not performed.

The vent air amount represents the amount of air bubbles which are stored in the apex portion of the blood filter housing when air bubbles are introduced to the blood filter at a certain blood flow rate. This item is used as an index of the ability of the blood filter to remove a relatively small amount of air bubbles.

The break-out threshold represents, as described above, a maximum amount of air bubbles which can be introduced at one time while maintaining the amount of microbubbles released from the blood outlet of the blood filter at a certain level or less (tolerable range). This item is used as an index of the ability of the blood filter to remove the air bubbles when a relatively large amount of air bubbles are introduced into the blood filter.

The pressure loss was measured in order to check whether or not the blood filter exhibits a pressure loss which is sufficiently acceptable for clinical use. It is preferable that the pressure loss is as low as possible, and the blood filter having a measured pressure loss of 80 mmHg or less is accepted for usual clinical use with no problem.

The vent air amount was measured in the following manner.

(1) A PVC tube 131 (FIG. 7) defined between the three-way stopcock 121 and the one-way stopcock 123 is filled with blood and weighed.

(2) The PVC tube 131 filled with the blood is connected to the experimental circuit as shown in FIG. 7.

(3) The centrifugal pump 101 is operated at a prescribed flow rate.

(4) A bypass tube 103 disposed parallel to the main tube 104 is closed at a prescribed position using a clamp 106, and a prescribed amount of air is injected from an air injection port 105.

(5) The clamp 106 is moved to the main tube 104, thereby introducing a prescribed amount of air to the blood filter 110.

(6) The air is temporarily stored in the apex portion of the blood filter housing.

(7) All the air bubbles temporarily stored in the apex portion of the blood filter housing are guided to the PVC tube 131.

(8) The amount of the PVC tube 131 containing the air bubbles is weighed.

(9) The vent air amount is calculated by the difference between the weight of the PVC tube 131 before the introduction of the air bubbles and the weight thereof after the introduction of the air bubbles.

The break-out threshold was measure in the following manner.

(1) The centrifugal pump 101 is operated at a prescribed flow rate.

(2) The bypass tube 103 disposed parallel to the main tube 104 is closed at a prescribed position using the clamp 106, and a prescribed amount of air is injected from the air injection port 105.

(3) The clamp 106 is moved to the main tube 104, thereby introducing a prescribed amount of air to the blood filter 110.

(4) The amount of microbubbles released from the blood filter is measured by the microbubble detection probe 111, thereby finding the break-out threshold.

The pressure loss was obtained in the, following maimer. The centrifugal pump 101 is operated at a prescribed flow rate in the experimental circuit shown in FIG. 7. The pressure loss is calculated based on the pressures measured by the pressure tranducers 107 and 108 connected to the inlet and the outlet of the blood filter.

Figure 8:
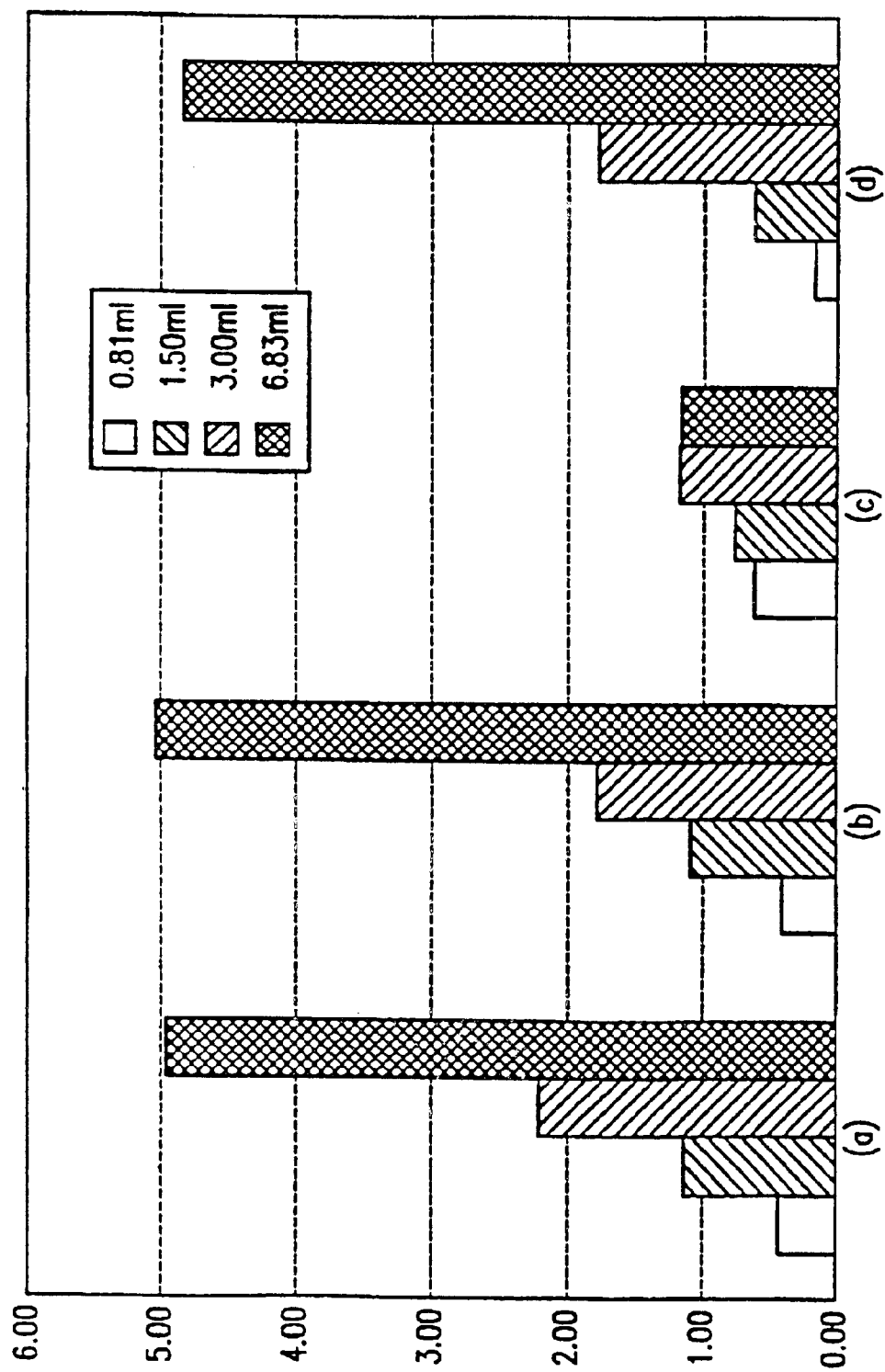
FIG. 8 is a graph illustrating the relative measurement results of the vent air amount of the blood filter according to the present invention and three conventional blood filters.

FIG. 8 shows the vent air amounts obtained. With reference to FIG. 8, line (a) represents the results of the blood filter according to the present invention, while lines (b), (c) and (d) represent the results of the conventional blood filters. In this test, air bubbles of four conventional amounts, i.e. 0.8 ml, 1.50 ml, 3.00 ml and 6.83 ml were injected from the air injection port 105 using a syringe having a prescribed capacity. The amount of air bubbles trapped in the apex portion of the blood filter housing was measured. The test was performed at a blood flow rate of 6 L/min. for all the blood filters.

As shown in FIG. 8, blood filter (a) according to the present invention exhibits a very satisfactory result with a higher vent air amount than those of the other blood filters with all the four conventional amounts, although blood filter (a) has the smallest total priming volume, i.e., 155 ml among the blood filters tested.

Blood filter (d), which is a conventional blood filter shown in FIG. 2 having a blood inlet in a bottom portion of the blood filter housing, has the largest total priming volume, i.e., 250 ml, among the four blood filters tested. However, blood filter (d) exhibits a slightly inferior result to blood filter (a) with all the four conventional amounts. In the case of blood filter (d), the decrease in the vent air amount is conspicuous especially when the amount of injected air bubbles is reduced. Such a result indicates that, as described above, it is difficult for the air bubbles to be separated from the blood flow whirling in the bottom portion of the blood filter housing due to a buoyancy of air being smaller than that of filter (a).

Blood filter (c), which is a conventional blood filter shown in FIG. 1 having a blood inlet in a top portion of the blood filter housing, exhibits an unsatisfactory result with a small vent air amount except when the amount of injected air bubbles is 0.81 ml. Such an undesirable result is caused by a drawback of this type of blood filter; i.e., a substantially nil capacity of the blood filter housing above the blood inlet due to the position of the blood inlet in the top portion of the blood filter housing.

Figure 9:
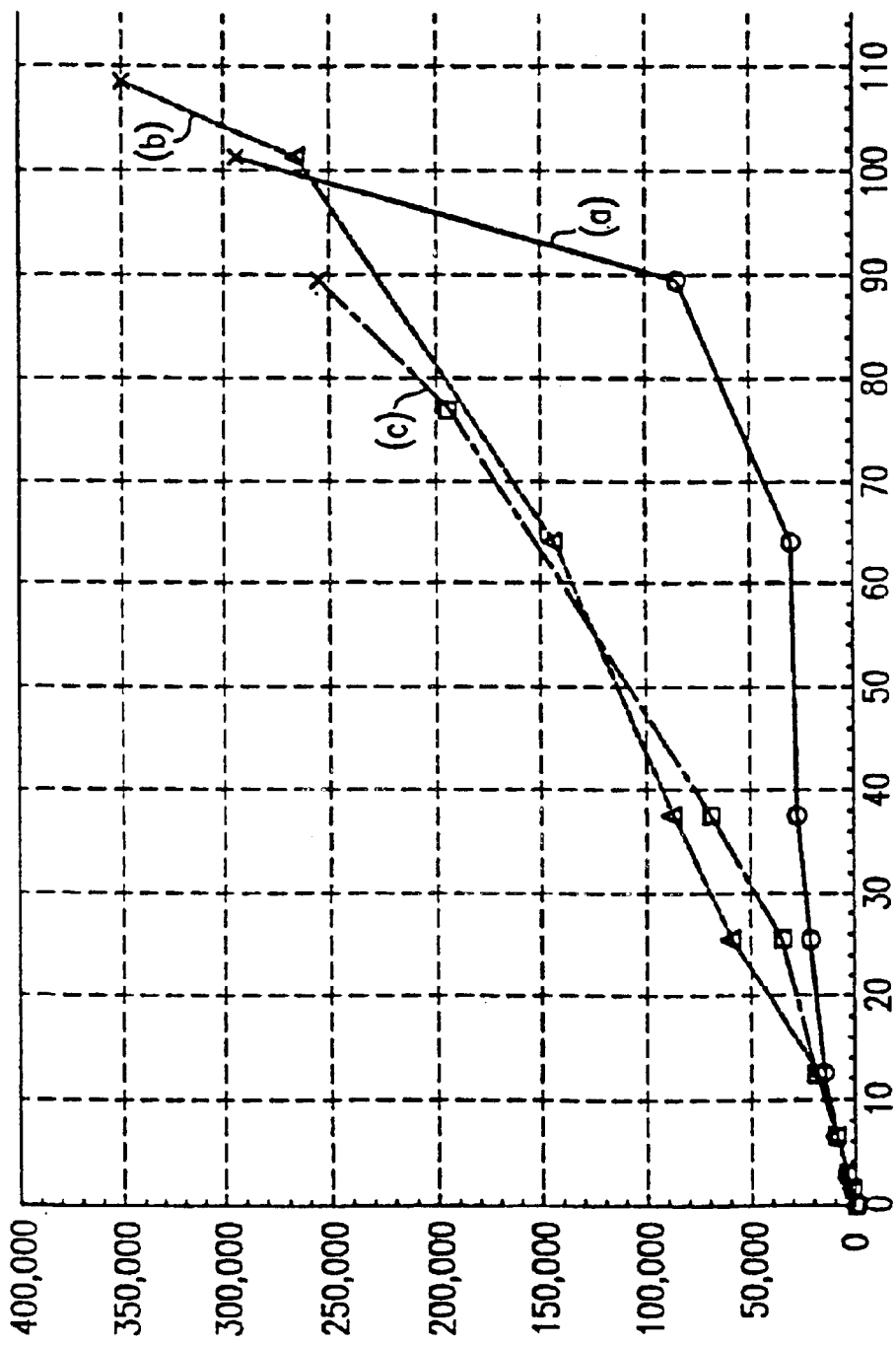
FIG. 9 is a graph illustrating the measurement results of the break-out threshold of the blood filter according to the present invention and two conventional blood filters.

FIG. 9 shows the break-out threshold of blood filters (a), (b) and (c). Again, line (a) represents the results of the blood filter according to the present invention, while lines (b) and (c) represent the results of the conventional blood filters. Plotted in FIG. 9 are the size and number of the microbubbles detected by the cardiovascular microbubble detector 112 (FIG. 7) and the total volume of the microbubbles calculated base on the size and number.

The break-out threshold was obtained by injecting air bubbles from the air injection port 105 in the experimental circuit shown in FIG. 7 using a syringe and measuring the amount of microbubbles released from the blood outlet of the blood filter. As the amount of injected air bubbles increases, the amount of released microbubbles gradually increases. When the amount of injected air bubbles exceed the break-out threshold, the amount of released microbubbles rapidly increases. Based on the phenomenon, the break-out threshold of the blood filter is obtained The test on the break-out threshold was performed at a blood flow rate of 7 L/min., and was not performed on blood filter (d) having a maximum blood flow rate of 6 L/min.

As can be appreciated from FIG. 9, blood filters (b) and (c) of the conventional type shown in FIG. 1 exhibit release of a considerable amount of microbubbles before the amount of injected microbubbles reaches the break-out threshold. As the amount of injected microbubbles increases, the amount of released microbubbles increases substantially linearly. This causes a danger to the patient in the actual extracorporeal circuit.

Blood filter (a) according to the present invention exhibits the most favorable characteristics; i.e., the amount of released microbubbles is suppressed to be minimum until the amount of injected air bubbles reaches the break-out threshold, and increases rapidly when the amount of injected air bubbles reaches the break-out threshold.

The break-out threshold obtained was 102 ml for blood filter (a), 109 ml for blood filter (b), and 90 ml for blood filter (c). It was confirmed that blood filter (a) according to the present invention has a break-out threshold which is equal to or greater than those of the other blood filters at a high blood flow rate of 7 L/min. despite the minimum priming volume of 155 ml.

Figure 10:
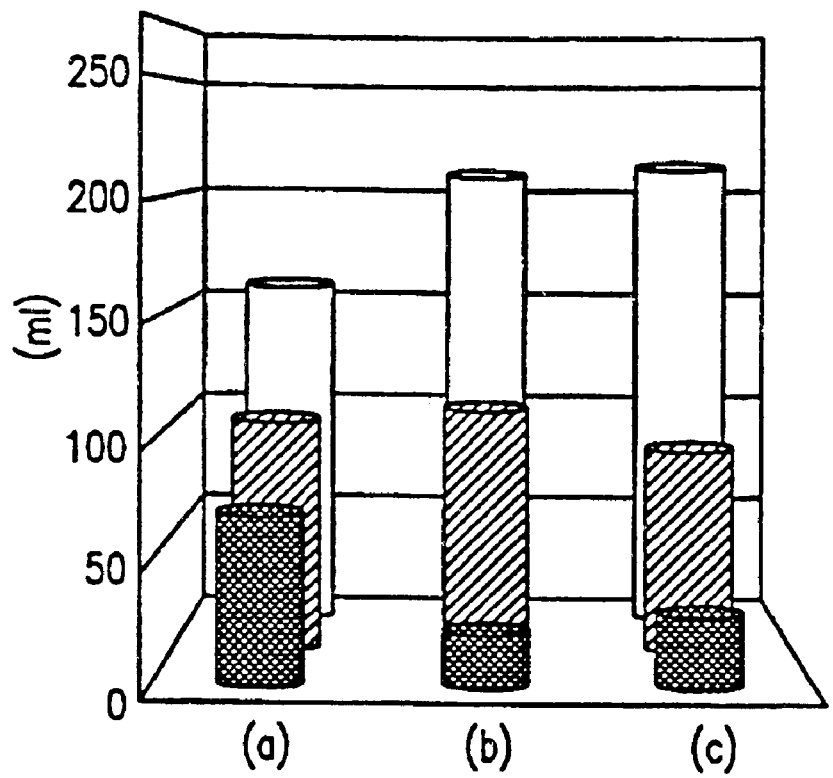
FIG. 10 is a graph illustrating the measurement results of the priming volume, the break-down threshold and the amount of the injected air bubbles when the amount of released microbubbles reaches 50,000 (10–8 ml) with respect to the blood filter according to the present invention and two conventional blood filters.

FIG. 10 and Table 3 show the break-out threshold shown in FIG. 9 from a different point of view. As in previous drawings, line (a) represents the results of the blood filter according to the present invention, and lines (b) and (c) represent the results of the conventional blood filters. The superiority of blood filter (a) over the conventional blood filters is demonstrated more clearly by FIG. 10 and Table 3. Shown in FIG. 10 and Table 3 are the performance of blood filters (a), (b) and (c) obtained based on the amount of air bubbles which is injected until the amount of microbubbles reaches a break-out threshold of 50,000 ($10^{-8}$ ml). This value of break-out threshold was set for the purpose of finding the variations of the amount of released microbubbles which are produced until the amount of injected air bubbles reaches the break-out threshold. Regarding this amount, blood filter (a) according to the present invention exhibits twice the value compared to the other blood filters, showing the superiority thereof.

Table 3 shows the ratio of the amount of the injected air bubbles (A) with respect to the priming volume of blood filter (C) when the amount of the released microbubbles reaches 50,000 ($10^{-8}$ ml), i.e., (A/C); and the ratio of the break-out threshold (B) with respect to the priming volume of the blood filter (C), i.e., (B/C).

TABLE 3

Performance comparison between the blood filter according to the present invention and the conventional blood filters.

| Blood Filter | (a) | (b) | (c) |
|---|---|---|---|
| (A) | 73 ml | 23 ml | 31 ml |
| (B) | 102 ml | 109 ml | 90 ml |
| (C) | 155 ml | 207 ml | 210 ml |
| A/C | 47% | 11% | 15% |
| B/C | 65% | 52% | 42% |

It is appreciated from Table 3 that the A/C value of blood filter (a) is about 4.3 and about 3.1 times larger than the values of blood filters (b) and (c), respectively, and that the B/C valve of blood filter (a)is about 1.25 and 1.5 times larger than the values of blood filters (b) and (c), respectively, although blood filter (a) has a priming volume of 155 ml, which is the minimum among the blood filters tested.

Blood filter (a) exhibits the maximum value among the blood filters tested in both A/C and B/C, showing that blood filter (a) has a high ability of removing air bubbles at a high flow rate despite the small size and capacity thereof.

Figure 11:
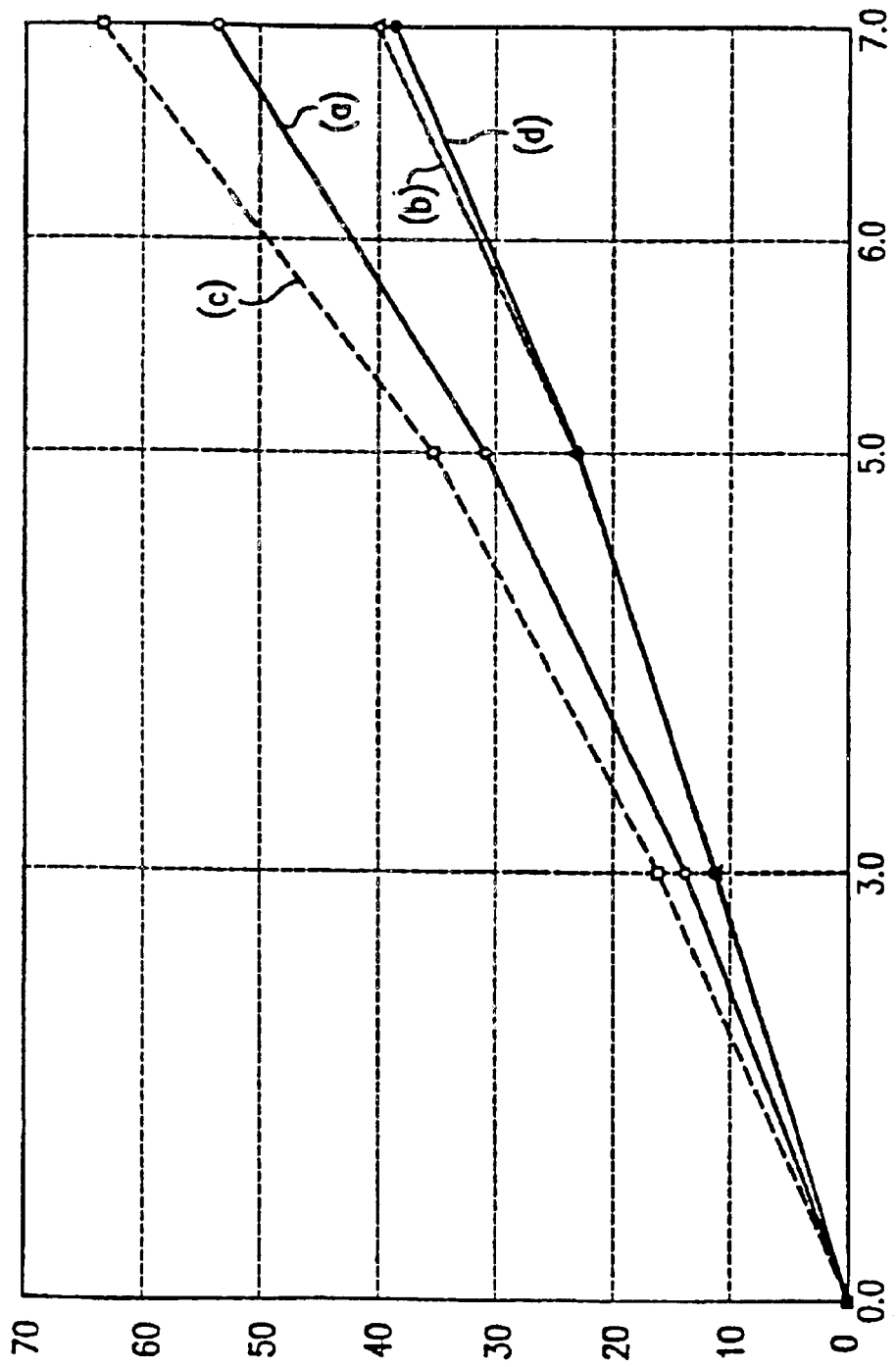
FIG. 11 is a graph illustrating the measurement results of the pressure loss with respect to the blood filter according to the present invention and three conventional blood filters.

FIG. 11 shows the pressure loss of blood filters (a), (b), (c) and (d). Line (a) represents the results of the blood filter according to the present invention, and lines (b), (c) and (d) represent the results of the conventional blood filters. Blood filter (d) has a maximum flow rate of 6 L//min. but is compared for reference. As illustrated in FIG. 11, blood filter (a) exhibits a pressure loss at a blood flow rate of 7 L/min. which is substantially intermediate among the blood filters tested, despite its minimum priming volume. Such a pressure loss of blood filter (a) is sufficiently acceptable for clinical use.

As various change could be made in the above constructions without departing from the scope of the present invention, it is intended that all matter contained in the above description or shown in the accompanying drawings shall be interpreted as illustrative and not limiting.

What is claimed is:

1. A blood filter comprising:
   a housing having an inner wall, an outer wall, a blood inlet, a blood outlet, and an air bubble outlet; and
   a filter element disposed in the housing, wherein the filter element divides an inner space of the housing into a first space which is in communication with the blood inlet, and a second space which is in fluid communication with the blood outlet, the first space includes a centre chamber defined within the inner wall of the housing and having the air bubble outlet, and a spiral chamber defined between the inner wall and the outer wall of the housing and extending upwardly along the inner wall of the housing;

wherein the spiral chamber has the blood inlet at one of the two ends thereof, an opening at the other end thereof which is in communication with the centre chamber, an inner bottom surface, and an inner top surface which together define a spiral passage extending from the blood inlet to the opening and disposed to substantially surround the centre chamber, and wherein the spiral passage of the spiral chamber increases in height from the blood inlet to the opening.

2. The blood filter according to claim 1, wherein the inner bottom surface of the spiral chamber extends along a perimeter of a bottom surface of the housing.

3. The blood filter according to claim 1 wherein an inner surface of the filter element which faces the second space and part of an inner surface of the housing define a lengthy passage which has the blood outlet at one end thereof and extends perpendicular to the inner bottom surface of the spiral chamber.

4. The blood filter according to claim 1, wherein the spiral passage of the spiral chamber surrounds the centre chamber in the range of 180 to 400 degrees.

5. The blood filter according to claim 1, wherein an apex of the inner top surface of tie spiral chamber is at a higher level that the filter element and is in the vicinity of the opening.

6. The blood filter according to claim 1, wherein the spiral chamber has a cross-section which increases from the blood inlet to the opening.

7. The blood filter according to claim 1, wherein the spiral passage of the spiral chamber has a cross-section which increases so that a blood velocity at the opening is ½ or less of a blood velocity at the blood inlet.

8. The blood filter according to claim 1, wherein the inner top surface of the spiral chamber extends from the blood inlet to the opening in a direction away from the inner bottom surface of the spiral chamber.

9. The blood filter according to claim 1, wherein the inner top surface of the spiral chamber extends upwardly at an angle in the range of 5° to 60° with respect to the inner bottom surface of the spiral chamber.

10. The blood filter according to claim 1, wherein the distance between an apex of the inner top surface of the spiral chamber in the vicinity of the opening and the inner bottom surface of the spiral chamber is 4 times or more the width of the spiral chamber in a radial direction of the housing.

11. The blood filter according to claim 1, wherein the centre chamber has a sub chamber, and the air bubble outlet is disposed in the sub chamber.

12. The blood filter according to claim 11, wherein the sub chamber has a volume which is $1/100$ to $1/10$ of the volume of the centre chamber.

13. The blood falter accords to claim 1, wherein the filter element is disposed in the centre chamber in such a manner that the centre axis of the filter element does not correspond to the centre chamber.

* * * * *